United States Patent [19]

Primus

[11] Patent Number: 4,737,453

[45] Date of Patent: Apr. 12, 1988

[54] SANDWICH IMMUNOASSAY UTILIZING A SEPARATION SPECIFIC BINDING SUBSTANCE

[75] Inventor: Frederick J. Primus, Pittstown, N.J.

[73] Assignee: Immunomedics, Inc., Newark, N.J.

[21] Appl. No.: 680,730

[22] Filed: Dec. 12, 1984

[51] Int. Cl.[4] .................. G01N 33/543; G01N 33/574; G01N 33/577

[52] U.S. Cl. .......................................... 435/5; 435/1; 435/810; 436/518; 436/548; 436/813; 436/822; 530/403; 530/807

[58] Field of Search .............. 436/501, 518, 531, 822, 436/813; 435/5, 7, 810; 530/403, 807

[56] References Cited

U.S. PATENT DOCUMENTS

| | | | |
|---|---|---|---|
| 4,134,792 | 1/1979 | Boguslaski et al. | 435/7 |
| 4,189,464 | 2/1980 | Blumberg et al. | 436/531 |
| 4,230,683 | 10/1980 | Decker et al. | 436/822 |
| 4,271,140 | 6/1981 | Bunting | 436/820 |
| 4,289,747 | 9/1981 | Chu | 435/7 |
| 4,298,685 | 11/1981 | Parikm et al. | 435/7 |
| 4,343,896 | 8/1982 | Wolters et al. | 435/7 |
| 4,371,515 | 2/1983 | Chu | 435/7 |
| 4,471,058 | 9/1984 | Smith et al. | 436/518 |
| 4,478,946 | 10/1984 | Van Der Merwe et al. | 436/518 |
| 4,496,654 | 1/1985 | Katz et al. | 435/7 |

OTHER PUBLICATIONS

E. Mizusawa et al, *Proc. Natl. Acad. Sci.* (U.S.A.) 79, 3011–3014, 1982.

C. R. Zeiss et al, *J. Immunol.* 110, 414–421, 1973.

*Primary Examiner*—Sidney Marantz
*Assistant Examiner*—David A. Saunders
*Attorney, Agent, or Firm*—Bernhard D. Saxe

[57] ABSTRACT

Immunoassay system for determining the amount of a polyvalent ligand in a liquid test sample, and based on:
(a) an insoluble phase to which is bound a separation specific binding substance which does not bind said ligand;
(b) a capture specific binding substance which specifically binds said ligand, and which is itself specifically bound by said spearation specific binding substance; and
(c) a probe specific binding substance which specifically binds said ligand at a site which is accessible when said ligand is bound to said capture specific binding substance, said probe specific binding substance being not substantially bound by said separation specific binding substance, and being detectable by at lease one detection procedure.

20 Claims, No Drawings

SANDWICH IMMUNOASSAY UTILIZING A SEPARATION SPECIFIC BINDING SUBSTANCE

BACKGROUND OF THE INVENTION

The present invention relates to a method and kit useful for determining the amount of a ligand in a liquid test sample.

Heterogeneous immunoassays for detection of a ligand in a liquid test sample have used a variety of methods to separate antigen complexed with antibody from free antigen. Some of these methods exploit physicochemical properties of the antigen, such as chemical solubility, molecular size, adsorption properties and electrophoretic mobility, whereas others employ immunological techniques in which an antibody which specifically binds the ligand-specific antibody (separation antibody) is used. Several known methods are based on the attachment of the anti-antigen antibody or the antigen itself to a solid phase such as polystyrene, the separation of components being effected by washing steps.

Examples of the variety of such immunoassays are found in, e.g., U.S. Pat. Nos. 4,228,237, 3,879,262, 4,021,534, 4,273,756, 4,098,876, 4,230,683, 4,048,298, 4,243,749, 4,343,896, 4,315,907, 4,332,783, 4,320,109, 4,298,685, 4,185,084, 4,312,944, to cite just a few typical examples. The disclosures of the foregoing patents are hereby incorporated herein by reference in their entireties. Although all of these methods are useful, each suffers from certain limitations, such as the need for purified antigen, the need to attach the antigen to a solid phase, the need for the antigen to have certain physicochemical properties, the use of multiple washing and incubating steps, and the like.

A need therefore continues to exist for a method and kit for immunoassays which avoids these disadvantages.

OBJECTS OF THE INVENTION

One object of the present invention is to provide an immunoassay method suitable for determining the amount of a polyvalent ligand in a liquid test sample, wherein the method can use a solid support that is adapted for use with any ligand, i.e., a "universal separation system".

Another object of the present invention is to provide an immunoassay method that avoids multiple washing and incubation steps.

A further object of the present invention is to provide an immunoassay method that can be used to effect simultaneous multiple antigen assays of a single liquid test sample.

Yet another object of the invention is to provide a test kit for use in effecting the method of the invention.

Other objects and advantages of the invention will become more readily apparent to those skilled in the art upon further study of the specification and appended claims.

SUMMARY OF THE INVENTION

These objects can be achieved by providing an immunoassay method for determining the amount of a polyvalent ligand in a liquid test sample, said ligand being an antibody or a substance capable of specific binding to an antibody, said method comprising the steps of:
(a) providing an insoluble phase to which is bound a separation specific binding substance which does not bind said ligand;
(b) incubating said insoluble phase with
  (1) said liquid test sample;
  (2) a capture specific binding substance which specifically binds said ligand, and which is itself specifically bound by said separation specific binding substance; and
  (3) a probe specific binding substance which specifically binds said ligand at a site which is accessible when said ligand is bound to said capture specific binding substance, said probe specific binding substance being not substantially bound by said separation specific binding substance, and being detectable by at least one detection procedure;
(c) separating said insoluble phase, after said incubation, from resultant liquid phase containing unbound reagents and components of said test sample; and
(d) determining, by means of said detection procedure, the amount of said detectable probe which is bound to said separated insoluble phase, or the amount of said detectable probe remaining is said resultant liquid phase, said determination being related to the amount of said ligand in said test sample.

The invention further provides an immunoassay kit for use in carrying out the foregoing method.

DETAILED DISCUSSION

A major advantage of the method and kit of the present invention is that the specific binding substance bound to the solid phase does not bind the ligand, but instead binds the capture specific binding substance. This permits considerable flexibility to be achieved which is not possible in other sandwich assay systems.

Where the ligand is a substance capable of binding specifically to an antibody but is not itself an antibody, i.e., the substance is a specific binding complement to the antibody, the capture specific binding substance will be an antibody which specifically binds the ligand. The separation specific binding substance bound to the solid phase will then be either an antibody that specifically binds the capture antibody, e.g., an isotype-specific or species-specific antibody, or an antibody that specifically binds a hapten that is conjugated to the capture antibody. Examples of the latter configuration can include a capture antibody that is conjugated to a hapten such as, e.g., a steroid, a fluorochrome, p-azobenzene arsenate, p-azotrimethylanilinium, benzoyl-L-glutamic acid, 2,4,6-trinitrophenyl and the like.

It will be understood that the term "antibody" as used herein means a polyclonal or monoclonal whole immunoglobulin, e.g., IgG, IgM, IgA, IgE and the like, or an immunoglobulin fragment, e.g., F(ab)2, F(ab')2, Fab, Fab' and the like, or a mixture thereof. Antibodies and antibody fragments which specifically bind a wide variety of ligands are known, and many of these are disclosed in the patents whose disclosures are incorporated herein by reference, such species being illustrative of representative genera. Many antibodies and antibody fragments which specifically bind tumor-associated markers are disclosed in, e.g., U.S. Pat. Nos. 4,348,376, 4,361,544, 4,331,647, 4,468,457, 4,444,744, 4,460,559 and 4,460,561, the disclosures of which are incorporated herein by reference, such antibodies and antibody fragments being illustrative of representative genera.

Other antibodies useful in the method and immunoassay kit of the invention are conventional and known to the art or can be produced by conventional immunological techniques, the particular method of preparation being within the ordinary skill of the art worker in light of the particular ligand to be assayed. For example, antibodies to enzymes, e.g., kinases such as creatinine kinase, dehydrogenases such as liver dehydrogenases and the like, hormones, e.g., luteinizing hormone, follicle stimulating hormone, steroids such as progesterone, testosterone and the like, virus or viral fragments, fungi, bacteria, protozoa or other disease causing or disease related microorganisms, can all be prepared and/or are known, and can be used as capture and/or probe antibodies in the method and kit of the present invention.

A particularly attractive type of hapten is a moiety containing a carborane ring system. Carboranes are not known to occur in natural biological samples such as serum, urine and the like, so that their use as haptens avoids the possibility of cross-reactivity with components of the test sample. Antibodies to carboranes can be developed by conventional techniques. Another attractive type of hapten is biotin, which would be used with avidin as the separation specific binding substance conjugated to the solid phase.

Use of any of the foregoing types of haptens permits the solid phase to function as a "universal" separation medium irregardless of the nature of the ligand or the capture specific binding substance. All that is required is that the capture species contain structural features that can be recognized by the separation specific binding substance, either by virtue of characteristic regions on an isotype, for example, or by virtue of the features of the hapten conjugated to the capture substance.

As an illustration, if the ligand to be determined is carcinoembryonic antigen (CEA), the capture specific binding substance is advantageously an antibody which specifically binds CEA, e.g., a polyclonal antiserum with high specific activity towards CEA, or a monoclonal antibody which specifically binds CEA. The probe would advantageously be another antiserum or monoclonal which specifically binds CEA, and which is conjugated to, e.g., a radioisotope, a flourescent marker, an enzyme or the like detectable moiety. For the sake of this illustration, the probe will be a monoclonal anti-CEA antibody to which is conjugated peroxidase. Again, for ease of illustration, the capture substance is either the same or a different anti-CEA monoclonal antibody to which is conjugated a diazophenylcarborane. The solid phase is a polypropylene test tube to which is conjugated monoclonal antibodies to the carborane ring of the hapten bound to the capture antibody.

The assay would proceed by adding an aliquot of the liquid test sample suspected to contain CEA, e.g., serum from a patient who has had surgery for removal of a colorectal tumor. To the sample would be added a solution of the capture and probe antibodies in a suitable medium, e.g., phosphate-buffered saline, and the resultant solution would be incubated for a period of time sufficient for binding the capture antibody to the solid phase, binding the ligand to the capture antibody and binding the probe antibody to the bound ligand. It will be understood that the reagents can be added sequentially as well as all together, and the order of their addition is not critical, although it may be advantageous to add the capture antibody first and the probe antibody afterwards rather than add these reagents in the inverse order.

Once the incubation is complete, hydrogen peroxide is added, together with o-phenylenediamine, and the activity of the peroxidase is determined spectrophotometrically, by conventional means. The activity can be correlated to the concentration of the enzyme, which in turn is related to the amount of CEA in the test sample by conventional means.

A simple variant of the above illustrated procedure could use I-125 as the label for the probe antibody. In this case, the tube would be drained after incubation and counted for bound radiolabel, which in turn would be related to the amount of CEA in the test sample.

Another simple variant would use biotin as the hapten conjugated to the capture antibody, and either an enzymatic or radioisotopic probe label. The solid phase would have avidin conjugated thereto, by conventional means, and any ligand bound by the capture antibody would be linked through the biotin-avidin couple to the solid phase and would be rendered detectable by the labeled probe bound to the ligand at a separately accessible site.

In order to use the method of this invention for the simultaneous determination of two or more ligands in the same test sample, the same hapten can be conjugated to a capture antibody for each ligand. For example, if it is desired to determine the amounts of both CEA and colon-specific antigen-p (CSAp), monoclonal antibodies to CEA and CSAp are each conjugated to, e.g., biotin, and the probe for CEA, another monoclonal which specifically binds CEA at a site which is accessible when CEA is bound to the capture antibody, is conjugated to, e.g., peroxidase while the probe antibody for CSAp, another monoclonal that specifically binds CSAp at a site which is accessible when CSAp is bound to the capture antibody, is labeled with, e.g., glucose oxidase. The test sample is then incubated with the solid phase, to which is bound avidin, and with the capture and probe antibodies, after which sequential determinations are effected with, e.g., hydrogen peroxide and o-phenylenediamine for the peroxidase determination, and with, e.g., glucose, o-dianisidine and peroxidase for the glucose oxidase determination, and the results correlated with standard curves.

Where the ligand is an antibody, it will often be convenient to use an anti-idiotype antibody as the capture or probe antibody, in conjunction with a probe or capture antibody that recognizes the isotype of the ligand antibody, each being conjugated with a function that can be bound by the separation specific binding substance on the solid phase or that can be detected, respectively. This avoids the need to use purified antigen as a component of the assay system. For example, if the ligand to be assayed is a human antibody to hepatitis-B surface antigen, the capture antibody could be a murine monoclonal anti-idiotype which specifically binds the hypervariable region of the ligand antibody and to which is conjugated a hapten such as a carborane moiety, while the probe antibody could be a goat anti-human Fab to which is conjugated I-125 in detectable quantities. The separation is effected by an anti-carborane antibody conjugated to the solid support, and the assay is effected by determining the amount of radioiodine bound to the solid support after incubation with the sample, in the presence of the capture and probe antibodies.

Immunoassay kits will normally contain a solid phase to which is bound the separation specific binding substance, e.g., polystyrene test tubes, microtiter plates and the like, coated with anti-hapten antibodies; lyophilized capture specific binding substances to which are conjugated haptens complementary to the separation specific binding substances, e.g., carborane-conjugated anti-ligand antibodies and the like; lyophilized probe specific binding substances labeled with detectable markers, e.g., enzyme-, radioisotope-, fluorescent marker-labeled anti-ligand antibodies and the like; ligand standards; and developers for the labels where necessary. Other conventional components can be included and these will be readily apparent to the skilled art worker.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Immunoassay for CSAp (A) Murine monoclonal antibodies to CSAp are prepared according to the method of U.S. Pat. No. 4,468,457, the disclosure of which is incorporated herein in its entirety by reference. This method involves producing a tryptic peptide having the immunological characteristics associated with native CSAp, by trypsin digestion under controlled conditions, using this tryptic peptide as an antigen, and generating murine monoclonal anti-CSAp IgG antibodies using conventional procedures.

(B) The antibodies prepared above are treated with a solution of p-(1,2-dicarbacloso-dodecaboranyl)benzenediazonium chloride, according to the method of Mizusawa et al., 1982, Proc. Nat. Acad. Sci., U.S.A., 79: 3011–3014, to introduce an average of 7 carborane groups onto the antibody. This can be done without significant loss of immunoreactivity, and further improvement can be attained by effecting the introduction of the carborane functions in the presence of the tryptic peptide to protect the hypervariable region of the antibody, after which the antigen is removed by the use of a chaotropic agent. After dialysis of the conjugate, e.g., normal saline at 4° C., the carborane-conjugated antibody is purified by affinity chromatography on a Sepharose 4B immunoadsorbent to which is bound the CSAp tryptic peptide.

(C) Monoclonal antibodies to the carborane moiety are prepared by conjugating the p-(1,2-dicarba-closododecaboranyl)benzenediazonium chloride to bovine serum albumin, injecting the conjugate into Balb/c mice, together with Freund's complete adjuvant, injecting the mice with boosters of the conjugate, and sacrificing the mice after 8 weeks. The spleens of the mice are excised and splenocytes are isolated, fused with murine myeloma cells, by conventional procedures, and clones isolated which secrete antibodies which specifically bind carborane moieties, as determined by enzyme immunoassay using carborane-goat IgG conjugates attached to the wells of microtiter plates.

(D) The anti-carborane antibodies prepared in part C are coated onto the inside of polystyrene test tubes according to the method disclosed in U.S. Pat. No. 4,185,084, the disclosure of which is incorporated herein by reference.

(E) Another monoclonal anti-CSAp antibody, prepared according to the procedure of U.S. Pat. No. 4,468,457, is conjugated to peroxidase, according to the procedure of Wilson and Nakane (1978), in "Immunofluorescence and Related Staining Techniques", Knapp et al., eds., pp. 215–224 (Elsevier/North Holland Biomedical Press, Amsterdam). This conjugate is used as the probe antibody for the assay.

(F) A liquid serum sample from a patient suspected of having colorectal cancer, is used as the test sample, after being freed of cellular matter by centrifugation. The sample is introduced into the polystyrene test tube prepared according to part D, and a solution of the capture and probe antibodies, prepared according to parts B and E, respectively, is introduced and incubated for 2 hours, at 37° C. The tube is washed with saline solution. A solution consisting of 0.08% o-phenylenediamine and 0.012% hydrogen peroxide in 0.1 M phosphate-citrate buffer, pH 5.0, is then introduced into the tube, and allowed to incubate for 30 minutes, at 20° C. The tube is then introduced into a spectrophotometer, and readings are taken at 490 nm. The peroxidase activity is determined, and correlated with CSAp content of the sample by the use of a standard curve, determined with a series of dilutions of known concentrations of the CSAp tryptic peptide.

EXAMPLE 2

Simultaneous Immunoassay for CSAp and CEA using Enzyme-labeled Probe Antibodies (A) Murine monoclonal antibodies to CEA are prepared according to Primus et al. (1983), Cancer Res., 43:686–692. This method involves the preparation of monoclonal antibodies against CEA purified from liver metastases of colonic adenocarcinoma and specificity characterization through reactivity with the cross-reactive antigens, nonspecific cross-reacting antigen and meconium antigen.

(B) The antibodies prepared above are labeled with carborane groups according to the procedure of part B of Example 1.

(C) Another monoclonal anti-CEA antibody, prepared as described in part A, but with a different epitope specificity than the anti-CEA antibody labeled with carborane groups, is conjugated to glucose oxidase as described in part E of Example 1.

(D) A liquid serum sample is placed into the polystyrene tube prepared according to part D of Example 1. Carborane-labeled anti-CSAP and anti-CEA monoclonal antibodies are then added to the tube along with peroxidase-labeled anti-CSAp and glucose oxidase-labeled anti-CEA monoclonal antibodies. The tube is incubated for 2 hours at 37° C. and then washed with saline solution. The CSAp content of the sample is determined using buffered o-phenylenediamine and hydrogen peroxide, as described in part F of Example 1, and the tube is again washed once with normal saline. A solution consisting of 1.67% glucose, 0.005% o-dianisidine and 0.0007% peroxidase in 0.05 M sodium acetate buffer, pH 5.1, is added and incubated for an additional 30 minutes at 22° C. to develop the glucose oxidase reaction. The tube is then introduced into a spectrophotometer and readings are taken at 490 nm. The glucose oxidase activity is determined, and correlated with CEA content of the sample by the use of a standard curve, determined with a series of dilutions of known concentrations of purified CEA.

EXAMPLE 3

Simultaneous Immunossays for CSAp and CEA using Radiolabeled Probe Antibodies A simultaneous assay is carried out as described in Example 2, except that instead of enzyme-labeled antibodies, I-125-labeled anti-CSAp and I-131-labeled anti-CEA monoclonal probe antibodies are used. CSAp and CEA quantities are correlated by differential measurement of the I-125 and I-131 radioactive levels in a two channel gamma scintillation counter.

EXAMPLE 4

Immunoassay Kit For Simultaneous Determinations of CEA And CSAp

A typical kit for effecting the simultaneous assay described in Example 2 would contain the following components:

polystyrene tubes coated with anti-carborane antibodies (dry). It will be understood that coated microtiter plates can be substituted for the tubes, or that lyophilized anti-carborane antibodies can be supplied for custom applications, e.g., coating of automated assay media.

lyophilized carborane-labeled anti-CEA and anti-CSAp antibodies.

lyophilized glucose-oxidase-labeled anti-CEA and peroxidase-labeled anti-CSAp antibodies.

lyophilized CEA and CSAp reference standards.

peroxidase developing system, e.g., in pellet form, containing o-phenylenediamine and buffer salts.

glucose oxidase developing system, e.g., in pellet form, containing peroxidase, o-dianisidine, glucose and buffer salts.

The user will normally provide distilled water, hydrogen peroxide and saline washing solution.

It will be understood that other configurations will be readily apparent to the skilled art worker, depending on the particular assay methods and instruments used. The foregoing kit is merely illustrative of a preferred embodiment.

The preceding examples can be repeated with similar success by substituting the generically or specifically described reactants and/or operating conditions of this invention for those used in the preceding examples. This includes the enzyme systems, hapten labels, radiolabels, fluorescent labels, solid supports, antibodies and the like described in the sources incorporated herein by reference as well as other conventional techniques and reagents.

From the foregoing description, one skilled in the art can easily ascertain the essential characteristics of this invention and, without departing form the spirit and scope thereof, can make various changes and modifications of the invention to adapt it to various usages and conditions.

What is claimed is:

1. An immunoassay method for determining the amount of a polyvalent ligand in a liquid test sample, said ligand being an antibody or a substance capable of specific binding to an antibody, said method comprising the steps of:
   (a) providing an insoluble phase to which is bound a separation specific binding substance which does not bind said ligand, wherein said separation specific binding substance is an antibody which specifically binds the carborane moiety of a hapten comprising a carborane moiety, said hapten being conjugated to a capture specific binding substance;
   (b) incubating said insoluble phase with
      (1) said liquid test sample;
      (2) a capture specific binding substance which specifically binds said ligand, and which is itself conjugated to said hapten comprising said carborane moiety which is specifically bound by said separation specific binding substance; and
      (3) a probe specific binding substance which specifically binds said ligand at a site which is accessible when said ligand is bound to said capture specific binding substance, said probe specific binding substance being not substantially bound by said separation specific binding substance, and being detectable by at least one direction procedure;
   (c) separating said insoluble phase, after said incubation, from resultant liquid phase containing unbound reagents and components of said test sample; and
   (d) determining, by means of said detection procedure, the amount of said detectable probe which is bound to said separated insoluble phase, or the amount of said detectable probe remaining in said resultant liquid phase, said determination being related to the amount of said ligand in said test sample.

2. The method of claim 1, wherein said ligand is an antibody, and said capture specific binding substance comprises a specific binding complement to said antibody.

3. The method of claim 1, wherein said probe specific binding substance is labeled with an enzyme, a radioisotope or a fluorescent marker.

4. The method of claim 1, wherein each of said probe specific binding substance and said capture specific binding substance comprises an antibody, and said ligand is a specific binding complement to both of said antibodies.

5. The method of claim 4, wherein said ligand is a tumor-associated marker.

6. The method of claim 5, wherein said marker is carcinoembryonic antigen, colon-specific antigen-p, human chorionic gonadotrophin or its beta-subunit, alpha-fetoprotein, meconium antigen or prostatic acid phosphatase.

7. The method of claim 4, wherein said ligand is an infectious organism.

8. The method of claim 7, wherein said infectious organism is a virus, bacterium, fungus or protozoan.

9. An immunoassay method for determining the amount of each of a plurality of polyvalent ligands in a liquid test sample, each of said ligands being an antibody or a substance capable of specific binding to an antibody, said method comprising the steps of;
   (a) providing an insoluble phase to which is bound at least one separation specific binding substance which does not bind any of said ligands, wherein each said separation specific binding substance is an antibody which specifically binds the carborane moiety of a hapten comprising a carborane moiety, said hapten being conjugated to a capture specific binding substance;
   (b) incubating said insoluble phase with
      (1) said liquid test sample;
      (2) for each said ligand, a capture specific binding substance which specifically binds said ligand, and which is itself conjugated to a hapten comprising a carborane moiety which is specifically bound by at least one of said separation specific binding substances; and (3) for each said ligand, a probe specific binding substance which specifically binds said ligand at a site which is accessible when said ligand is bound to said capture specific binding substance, each said probe specific binding substance being not substantially bound by said separation specific binding substance, and each being separately detectable by at least one detection procedure;

(c) separating said insoluble phase, after said incubation, from resultant liquid phase containing unbound reagents and components of said test sample; and (d) determining, by means of said detection procedure, the amount of each said detectable probe which is bound to said separated insoluble phase, or the amount of each said detectable probe remaining in said resultant liquid phase, said determination being related to the amount of said ligand in said test sample.

10. The method of claim 9, suitable for the simultaneous determination of CEA and CSAp, wherein one of said capture specific binding substances and one of said probe specific binding substances are each a monoclonal antibody which specifically binds CEA, and a different one of said capture specific binding substances and a different one of said probe specific binding substances are each a monoclonal antibody which specifically binds CSAp.

11. An immunoassay kit, suitable for determining the amount of a polyvalent ligand in a liquid test sample, comprising:
(a) an insoluble phase to which is bound a separation specific binding substance which does not bind said ligand, wherein said separation specific binding substance is an antibody which specifically binds the carborane moiety of a hapten comprising a carborane moiety, said hapten being conjugated to a capture specific binding substance;
(b) a capture specific binding substance which specifically binds said ligand, and which is itself conjugated to said hapten comprising said carborane moiety which is specifically bound by said separation specific binding substance; and
(c) a probe specific binding substance which specifically binds said ligand at a site which is accessible when said ligand is bound to said capture specific binding substance, said probe specific binding substance being not substantially bound by said separation specific binding substance, and being detectable by at least one detection procedure.

12. The kit of claim 11, suitable for use wherein said ligand is an antibody, wherein said capture specific binding substance comprises an antigen which is a specific binding complement to said antibody.

13. The kit of claim 11, wherein said probe specific binding substance is labeled with an enzyme, a radioisotope or a fluorescent marker.

14. The kit of claim 11, wherein each of said probe specific binding substance and said capture specific binding substance comprises an antibody which specifically binds the ligand to be assayed.

15. The kit of claim 14 suitable for use for immunoassay of a ligand which is a tumor-associated marker, wherein said capture specific binding substance and said probe specific binding substance each comprise an antibody which specifically binds the tumor-associated marker to be assayed.

16. The kit of claim 15 wherein said marker is carcinoembryonic antigen, colon-specific antigen-p, human chorionic gonadotrophin or its beta-subunit, alpha-fetoprotein, meconium antigen or prostatic acid phosphatase.

17. The kit of claim 14, wherein said capture and probe antibodies each specifically bind an infectious organism.

18. The kit of claim 17, wherein said infectious organism is a virus, bacterium, fungus or protozoan.

19. An immunoassay kit, suitable for determining the amount of each of a plurality of polyvalent ligands in a liquid test sample, each of said ligands being an antibody or a substance capable of specific binding to an antibody, said kit comprising;
(a) an insoluble phase to which is bound at least one separation specific binding substance which does not bind any of said ligands, wherein each said separation specific binding substance is an antibody which specifically binds the carborane moiety of a hapten comprising a carborane moiety, said hapten being conjugated to a capture specific binding substance;
(b) for each said ligand, a capture specific binding substance which specifically binds said ligand, and which is itself conjugated to a hapten comprising a carborane moiety which is specifically bound by at least one of said separation specific binding substances; and
(c) for each said ligand, a probe specific binding substance which specifically binds said ligand at a site which is accessible when said ligand is bound to said capture specific binding substance, each said probe specific binding substance being not substantially bound by said separation specific binding substance, and each being separately detectable by at least one detection procedure.

20. The kit of claim 19, suitable for the simultaneous determination of CEA and CSAp, wherein one of said capture specific binding substances and one of said probe specific binding substances are each a monoclonal antibody which specifically binds CEA, and a different one of said capture specific binding substances and a different one of said probe specific binding substances are each a monoclonal antibody which specifically binds CSAp.

* * * * *